(12) United States Patent
Keady

(10) Patent No.: US 11,389,333 B2
(45) Date of Patent: Jul. 19, 2022

(54) EARPLUG AND PUMPING SYSTEMS

(71) Applicant: Staton Techiya LLC, Delray Beach, FL (US)

(72) Inventor: John P. Keady, Fairfax Station, VA (US)

(73) Assignee: Staton Techiya, LLC, Delray Beach, FL (US)

( * ) Notice: Subject to any disclaimer, the term of this patent is extended or adjusted under 35 U.S.C. 154(b) by 95 days.

(21) Appl. No.: 16/920,425

(22) Filed: Jul. 3, 2020

(65) Prior Publication Data

US 2020/0330282 A1    Oct. 22, 2020

Related U.S. Application Data

(63) Continuation of application No. 14/860,617, filed on Sep. 21, 2015, now abandoned, which is a
(Continued)

(51) Int. Cl.
*A61F 11/10* (2006.01)
*A61F 11/08* (2006.01)
(Continued)

(52) U.S. Cl.
CPC .............. *A61F 11/10* (2013.01); *A61F 11/00* (2013.01); *A61F 11/08* (2013.01); *A61M 25/10181* (2013.11); *H04R 1/1083* (2013.01)

(58) Field of Classification Search
CPC .... A61F 2011/085; A61F 11/06; A61F 11/08; A61F 11/10; A61F 11/12; H04R 1/1083; A61M 25/10181
See application file for complete search history.

(56) References Cited

U.S. PATENT DOCUMENTS 3,876,843 A    4/1975    Moen
4,020,297 A    4/1977    Brodie
(Continued)

FOREIGN PATENT DOCUMENTS

CN    107071123    8/2017
EP    2190391 B1    6/2010
(Continued)

OTHER PUBLICATIONS

Olwal, A. and Feiner S. Interaction Techniques Using Prosodic Features of Speech and Audio Localization. Proceedings of IUI 2005 (International Conference on Intelligent User Interfaces), San Diego, CA, Jan. 9-12, 2005, p. 284-286.
(Continued)

*Primary Examiner* — Camtu T Nguyen
(74) *Attorney, Agent, or Firm* — Akerman LLP; Peter A. Chiabotti

(57) ABSTRACT

An earpiece, earphone, earbud or earplug includes an inflatable element operatively attached to a distal end by an inflation channel, and an anti-distal end of the inflation channel that provides a pressuring force via fluid transfer of a fluid to maintain an expansion of the inflatable element. The inflatable element can be pressurized to a gauge pressure range between 0.05 bar and 3.0 bar. In some embodiments, the inflatable element is pressurized to a gauge pressure range from 0.3 bar to 0.25 bar and maintains such gauge pressure range for at least 12 hours. In some embodiments, the inflatable element uses a material of a predetermined permeability for a given density of fluid and a given thickness of the inflatable element such that an inflation pressure drops from 1.2 atmospheres to 1 atmospheres in 8 hours after the inflatable element is pressurized to 1.2 atmospheres. Other embodiments are disclosed.

13 Claims, 5 Drawing Sheets

Related U.S. Application Data continuation of application No. 13/201,308, filed as application No. PCT/US2010/024308 on Feb. 16, 2010, now Pat. No. 9,138,353.

(60) Provisional application No. 61/152,545, filed on Feb. 13, 2009.

(51) Int. Cl.
  *A61F 11/00* (2022.01)
  *A61M 25/10* (2013.01)
  *H04R 1/10* (2006.01)

(56) References Cited

U.S. PATENT DOCUMENTS

| | | |
|---|---|---|
| 4,054,749 A | 10/1977 | Suzuki et al. |
| 4,060,080 A * | 11/1977 | Akiyama ............. A61F 11/10 128/865 |
| 4,088,849 A | 5/1978 | Usami et al. |
| 4,947,440 A | 8/1990 | Bateman et al. |
| 5,138,722 A | 8/1992 | Urella |
| 5,142,587 A | 8/1992 | Kobayashi |
| 5,208,867 A | 5/1993 | Stites, III |
| 5,267,321 A | 11/1993 | Langberg |
| 5,319,163 A | 6/1994 | Scott |
| 5,524,056 A | 6/1996 | Killion et al. |
| 5,712,453 A | 1/1998 | Bungardt |
| 5,764,781 A | 6/1998 | Ding |
| 5,903,868 A | 5/1999 | Yuen et al. |
| 6,021,207 A | 2/2000 | Puthuff et al. |
| 6,021,325 A | 2/2000 | Hall |
| 6,163,338 A | 12/2000 | Johnson et al. |
| 6,163,508 A | 12/2000 | Kim et al. |
| 6,226,389 B1 | 5/2001 | Lemelson et al. |
| 6,298,323 B1 | 10/2001 | Kaemmerer |
| 6,321,070 B1 | 11/2001 | Clark |
| 6,359,993 B2 | 3/2002 | Brimhall |
| 6,400,652 B1 | 6/2002 | Goldberg et al. |
| 6,415,034 B1 | 7/2002 | Hietanen |
| 6,567,524 B1 | 5/2003 | Svean et al. |
| RE38,351 E | 12/2003 | Iseberg et al. |
| 6,661,901 B1 | 12/2003 | Svean et al. |
| 6,728,385 B2 | 4/2004 | Kvaloy et al. |
| 6,748,238 B1 | 6/2004 | Lau |
| 6,750,295 B2 | 6/2004 | Albano |
| 6,754,359 B1 | 6/2004 | Svean et al. |
| 6,804,638 B2 | 10/2004 | Fiedler |
| 6,804,643 B1 | 10/2004 | Kiss |
| 7,072,482 B2 | 7/2006 | Van Doorn et al. |
| 7,107,109 B1 | 9/2006 | Nathan et al. |
| 7,209,569 B2 | 4/2007 | Boesen |
| 7,430,299 B2 | 9/2008 | Armstrong et al. |
| 7,433,714 B2 | 10/2008 | Howard et al. |
| 7,450,730 B2 | 11/2008 | Bertg et al. |
| 7,477,756 B2 | 1/2009 | Wickstrom et al. |
| 7,562,020 B2 | 6/2009 | Le et al. |
| 7,688,983 B2 | 3/2010 | Voix |
| 7,756,285 B2 | 7/2010 | Sjursen et al. |
| 7,778,434 B2 | 8/2010 | Juneau et al. |
| 7,801,318 B2 | 9/2010 | Barthel |
| 7,920,557 B2 | 4/2011 | Moote |
| 8,014,553 B2 | 9/2011 | Radivojevic et al. |
| 8,401,200 B2 | 3/2013 | Tiscareno |
| 8,493,204 B2 | 7/2013 | Wong et al. |
| 8,550,206 B2 | 10/2013 | Keady |
| 8,774,433 B2 | 7/2014 | Goldstein |
| 8,774,435 B2 | 7/2014 | Ambrose |
| 9,037,458 B2 | 5/2015 | Park et al. |
| 9,084,060 B2 | 7/2015 | Liu |
| 9,123,343 B2 | 9/2015 | Kurki-Suonio |
| 9,135,797 B2 | 9/2015 | Couper et al. |
| 9,293,128 B2 | 3/2016 | Goldstein |
| 2001/0046304 A1 | 11/2001 | Rast |
| 2002/0106091 A1 | 8/2002 | Furst et al. |
| 2002/0118798 A1 | 8/2002 | Langhart et al. |
| 2003/0161097 A1 | 8/2003 | Le et al. |
| 2003/0165246 A1 | 9/2003 | Kvaloy et al. |
| 2004/0042103 A1 | 3/2004 | Mayer |
| 2004/0109668 A1 | 6/2004 | Stuckman |
| 2004/0125965 A1 | 7/2004 | Alberth, Jr. et al. |
| 2004/0190737 A1 | 9/2004 | Kuhnel et al. |
| 2004/0196992 A1 | 10/2004 | Ryan |
| 2004/0203351 A1 | 10/2004 | Shearer et al. |
| 2005/0078838 A1 | 4/2005 | Simon |
| 2005/0123146 A1 | 6/2005 | Voix et al. |
| 2005/0288057 A1 | 12/2005 | Lai et al. |
| 2006/0067551 A1 | 3/2006 | Cartwright et al. |
| 2006/0083395 A1 | 4/2006 | Allen et al. |
| 2006/0092043 A1 | 5/2006 | Lagassey |
| 2006/0195322 A1 | 8/2006 | Broussard et al. |
| 2006/0204014 A1 | 9/2006 | Isenberg et al. |
| 2007/0043563 A1 | 2/2007 | Comerford et al. |
| 2007/0086600 A1 | 4/2007 | Boesen |
| 2007/0189544 A1 | 8/2007 | Rosenberg |
| 2007/0291953 A1 | 12/2007 | Ngia et al. |
| 2008/0037801 A1 | 2/2008 | Alves et al. |
| 2008/0165988 A1 | 7/2008 | Terlizzi et al. |
| 2009/0010456 A1 | 1/2009 | Goldstein et al. |
| 2009/0024234 A1 | 1/2009 | Archibald |
| 2010/0061564 A1 | 3/2010 | Clemow et al. |
| 2010/0296668 A1 | 11/2010 | Lee et al. |
| 2011/0096939 A1 | 4/2011 | Ichimura |
| 2011/0264447 A1 | 10/2011 | Visser et al. |
| 2011/0293103 A1 | 12/2011 | Park et al. |
| 2013/0177179 A1 | 7/2013 | Ambrose |
| 2014/0247948 A1 | 9/2014 | Goldstein |
| 2014/0247952 A1 | 9/2014 | Goldstein |
| 2016/0104452 A1 | 4/2016 | Guan et al. |
| 2018/0176681 A1 | 6/2018 | Asada |

FOREIGN PATENT DOCUMENTS

| | | |
|---|---|---|
| EP | 1519625 A2 | 8/2010 |
| WO | 2006037156 A1 | 4/2006 |

OTHER PUBLICATIONS

Bernard Widrow, John R. Glover Jr., John M. McCool, John Kaunitz, Charles S. Williams, Robert H. Hearn, James R. Zeidler, Eugene Dong Jr, and Robert C. Goodlin, Adaptive Noise Cancelling: Principles and Applications, Proceedings of the IEEE, vol. 63, No. 12, Dec. 1975.

Mauro Dentino, John M. McCool, and Bernard Widrow, Adaptive Filtering in the Frequency Domain, Proceedings of the IEEE, vol. 66, No. 12, Dec. 1978.

* cited by examiner

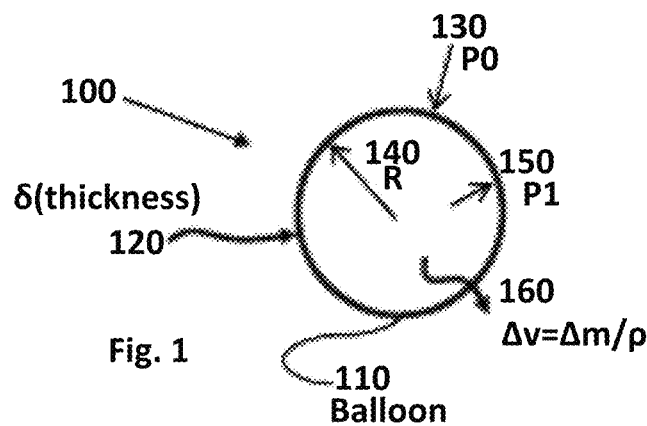
Fig. 1
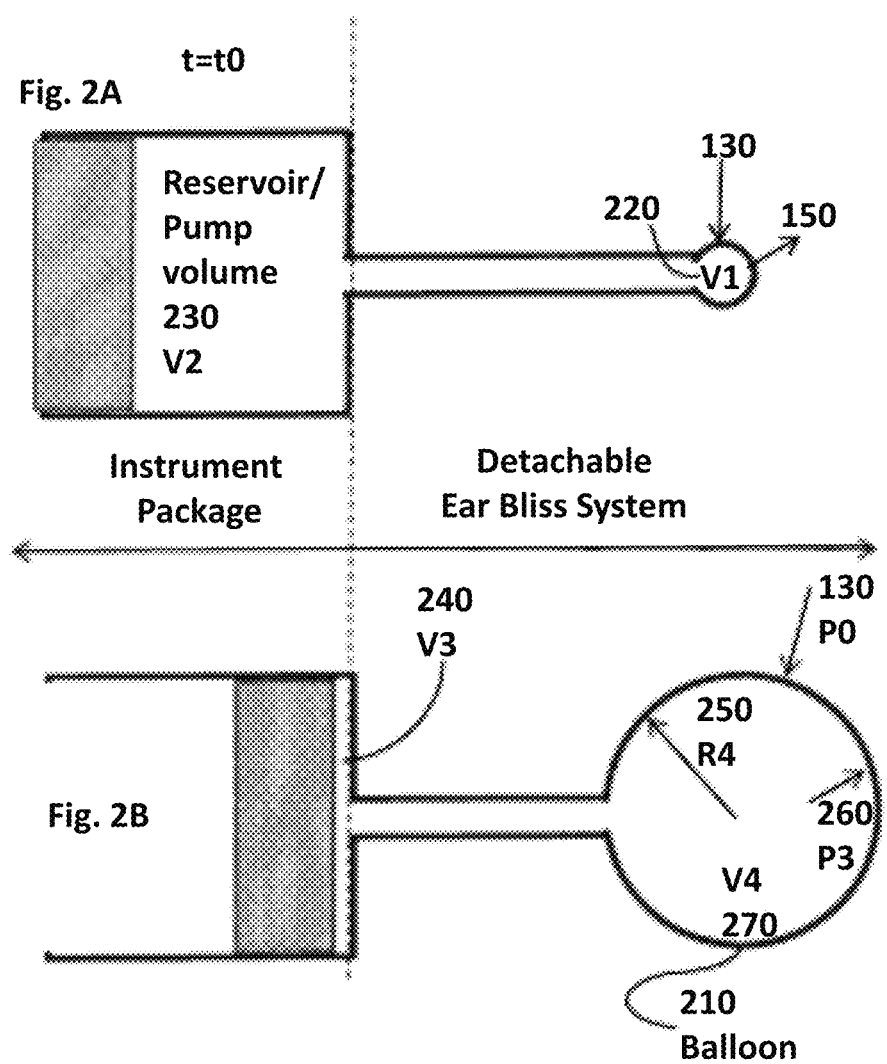
Fig. 2A
Fig. 2B

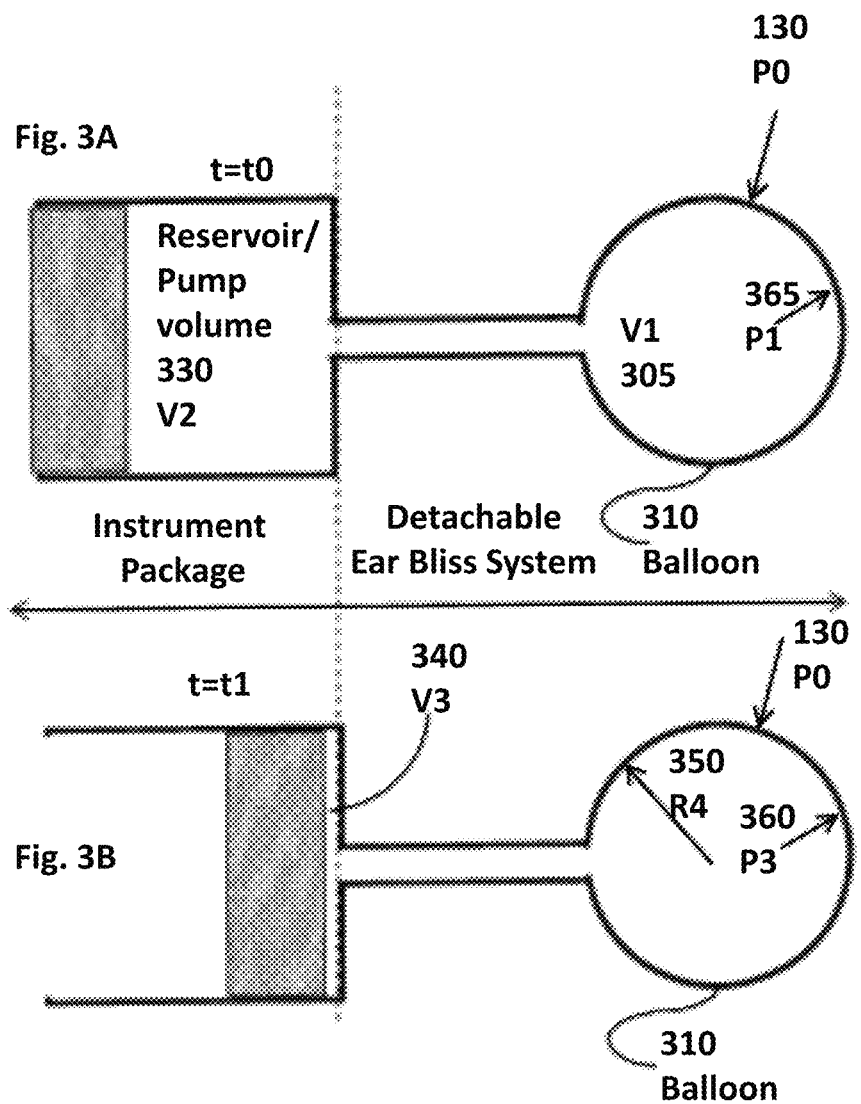

EARPLUG AND PUMPING SYSTEMS

CROSS-REFERENCE TO RELATED APPLICATIONS

This application is a continuation of U.S. patent application Ser. No. 14/860,617, filed Sep. 21, 2015, which is a continuation of U.S. patent application Ser. No. 13/201,308 filed Jan. 19, 2012, which is a U.S. National Phase Application of PCT International Application No. PCT/US2010/024308 filed Feb. 16, 2010 which claims the benefit of U.S. provisional patent application No. 61/152,545 filed on Feb. 13, 2009, the disclosures of which are incorporated herein by reference in their entireties.

FIELD

The embodiments relate in general to devices and methods of earphone, earpiece, earbud, fit and sealing technology, and particularly though not exclusively, is related to earplug and pumping systems for earplugs.

BACKGROUND

Earplugs are currently rated with an EPA governed Noise Reduction Rating (NRR). The Noise Reduction Rating (NRR) is the measurement, in decibels, of how well a hearing protector reduces noise as specified by human subject testing as regulated by the Environmental Protection Agency. The higher the NRR number the greater the noise reduction.

Earplug fit affects the effective noise reduction ratio of an earplug. For example one study illustrated that a good fit of the earplug has an NRR of 33 dB, while the same earplug fitted poorly provided an NRR of OdB.

In the industrial noise environment the use of hearing protection is paramount. The correct fit of the hearing protection often determines its usefulness. Thus the fit of an earplug is important. Current earplugs have various levels of ease of fit. Professional training can increase the effectiveness of earplug fit, however many users do not have access to professional training. Thus a system that improves the chance of improved fitting will be beneficial to protecting hearing in many users.

Several systems have been developed in the past. For example: Wasserman (U.S. Pat. No. 2,876,767) illustrates (FIG. 7, U.S. Pat. No. 2,876,767) a system requiring an external pump to inflate an inflatable bladder as does Pierre (FIG. 5, U.S. Pat. No. 4,896,679); Rose (U.S. Pat. No. 4,089,332, FIGS. 1-2) illustrates an earplug 10 with a first end 14, that when deformed into a second stable position results in the extension of a second end, the system lacking a method for maintaining a pressurizing force, thus lending itself to possible de-inflation; Krause (U.S. Pat. No. 5,483,027) illustrates a bi-directionally inserted earplug with a two-way valve to maintain a chamber in an expanded condition, while Michael et al. (U.S. Pat. No. 2,824,558) illustrates an earplug with a one-way valve.

Unlike related art, a simplified system (for ease of adoption) designed for use in a particular and adjustable pressure range to provide the necessary sound isolation would be useful.

SUMMARY

At least one exemplary embodiment is related to an earplug comprising: at least a partially flexible distal end; an inflatable element; and a flexible anti-distal end, where the anti-distal end has at least one portion that is deformable, where the inflatable element is operatively attached to the distal end by an inflation channel, where when the at least one portion is deformed the inflatable element expands to an adjustable pressure, where at least one portion of the anti-distal end provides a pressurizing force to maintain the expansion of the inflatable element.

At least one exemplary embodiment provides the pressurizing force using an elastic membrane.

At least one exemplary embodiment provides the pressurizing force using a plate secured by screwing in the plate to a given position.

At least one exemplary embodiment provides the pressurizing force using a resilient member.

Further areas of applicability of embodiments of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

Exemplary embodiments of the present invention will become more fully understood from the detailed description and the accompanying drawings, wherein:

FIG. 1 illustrates a generic illustration of an inflatable element;

FIGS. 2A and 2B illustrate a generic variable volume inflatable element attached to a reservoir and a stent;

FIGS. 3A and 3B illustrate a generic constant volume inflatable element attached to a reservoir and a stent;

DETAILED DESCRIPTION OF EXEMPLARY EMBODIMENTS

Figure 4A:
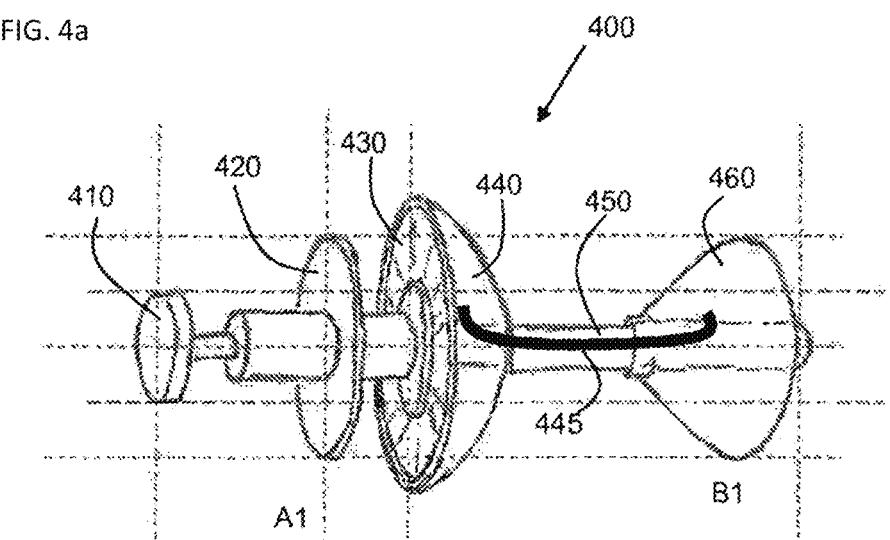
FIGS. 4a and 4b illustrate an earplug including an inflatable element attached to a reservoir and a stent, where an elastic membrane provides a pressurizing force in accordance with at least one exemplary embodiment.

The following description of exemplary embodiment(s) is merely illustrative in nature and is in no way intended to limit the invention, its application, or uses.

Processes, methods, materials and devices known by one of ordinary skill in the relevant arts may not be discussed in detail but are intended to be part of the enabling discussion where appropriate. For example material used for flexible members of various durometer, elastic membrane material, balloon material, may not be specified but are known by one of ordinary skill by earpiece, hearing aid, earplug, and medical angioplasty manufacturers.

Additionally, the size of structures used in exemplary embodiments are not limited by any discussion herein (e.g., the sizes of structures can be macro (millimeter, centimeter, meter, size), micro (micro meter), nanometer size and smaller), and can be used in various orifices besides ear canals although ear canals will be discussed.

The materials used for earplug construction will not be discussed in detail, however any materials, as known by one of ordinary skill in the art of earplug manufacturing and medical balloon manufacturing, can be used to fabricate earplugs in accordance with exemplary embodiments of the present invention. For example Lucite, ultraviolet resin, polyethylene, soft acrylic, soft ultra-violet silicone, polyvinyl chloride, medical polymers, foam, can all be used for various portions of the earplug construction.

At least one exemplary embodiment is directed to an earplug comprising: at least a partially flexible distal end; an inflatable element; and a flexible anti-distal end, where the anti-distal end has at least one portion that is deformable, where the inflatable element is operatively attached to the distal end by an inflation channel, where when the at least one portion is deformed the inflatable element expands to an adjustable pressure, where at least one portion of the anti-distal end provides a pressurizing force to maintain the expansion of the inflatable element.

The distal end can include a flexible and inflexible portion. The flexible portion can be an elastic membrane for example an elastic membrane that can be stretched to several initial lengths then returned to its original size. Many materials can be used (e.g., silicon) that provide a restoring force when deformed (e.g., stretched). Typically such materials have a lower Durometer (e.g., less than 50 Shore).

The inflexible portion can be made of less stretchable material, for example when stretched to less than 100% the material returns to its shape, for example typically such materials have a higher Durometer (e.g., greater than 50 Shore).

The flexible portion can also be a compressible or expandable bladder operatively attached to the inflexible portion.

The deformable portion of the anti-distal end can be any deformable portion of the anti-distal end for example it can be a bladder, or a deformable dome of the anti-distal end, where deformation moves fluid from one section into the inflatable element.

The inflatable element can be any element that can be inflated for example a self contained bladder or balloon, or a sheath around a stent that can expand away from the stent.

The inflatable element can be operatively attached to the distal end by an inflation channel. The inflation channel can be a tube carrying fluid from the anti-distal end to the inflation element, or can be a channel for example within a stent.

The inflatable element can be pressurized via fluid transfer into the inflatable element. For example deformation of a portion of the anti-distal end moves fluid from a chamber (e.g. a bladder) through an inflation channel into the inflation element. A pressure can be chosen (e.g., by deforming a portion of the anti-distal end by a given amount) for the gauge pressure inside the inflation element. Note that the fluid can be water, air, or any type of fluid and gas that provides the requisite time of pressurization. For example if the inflation element is to be pressurized from 0.30 bar gauge pressure to 0.25 bar gauge pressure for 12 hours, then the material requirement for the inflation element and other pneumatic systems can be determined (e.g., the inflation channel can also be designed to reduce permeability within the given limits). Thus in the non-limiting example above a material can be chosen to provide the necessary permeability for the given fluid used (e.g., Teflon for air for 12 hours or more for an inflation element that maintains gauge pressure from 0.30 bar gauge pressure to 0.25 bar gauge pressure).

In accordance with at least one exemplary embodiment a pressurizing force can be applied to the pneumatic system (e.g., bladder in the anti-distal end, the inflation channel and the inflation element). For example a screwed in plate can press against an anti-distal end bladder deforming it increasing the pressure in the pneumatic system, where the thread force maintains the pressurizing force. Additionally other systems can provide the pressurizing force, for example an elastic membrane can provide a restoring force. For example one can pre-pressurize a closed pneumatic system to the desired gauge pressure, then one end pulled (e.g., a plate attached to an elastic membrane pulled), pulling the fluid out of the inflation element, where when the pulling action is released the elastic membrane provides a restoring force that forces the fluid back into the inflation element.

A further exemplary embodiment can use a resilient member to provide a restoring force when deformed. For example a plastic clip can be pulled then released to return to its original shape. In at least one exemplary embodiment a resilient member in the form of an opened plastic clip presses against a bladder, so that when the plastic clip is pinched it closes around a stent and the bladder is free to fill, which if coupled to an inflation element will inflate the inflation element. The volume of the deformation can be calculated to provide the requisite inflation element pressure.

The inflatable element can be a sheath around a stent, where a hole in the stent allows fluid to flow into the sheath stretching the sheath until the orifice in which the sheath is placed is obstructed or occluded. The inflation element can also be a balloon attached to a stent that is inflated or deflated. The inflation element can be made of various elastic materials. Additionally the inflatable element can be a non-elastic material that is preformed to a size and shape when inflated. For example a variable volume balloon can be tight against the stent when deflated. When inflated it can expand until a predesigned shape is obtained, for example by varying the thickness of the balloon along the stent direction. For example a constant volume balloon can be preformed into a shape (e.g., a cone).

The inflatable element can be pressurized to a range of gauge pressures (pressure difference between inside the inflation element and outside the inflation element). For example the inflatable element can be pressurized to a gauge pressure range between 0.05 bar and 3.0 bar. The pressurized inflation element can provide sound isolation when the inflation element occludes an orifice (e.g., ear canal).

FIG. 1 illustrates a generic illustration of an inflatable element 100 including balloon 110. The permeability $\varepsilon$ can be expressed in terms of radius 140R, the internal pressure 150 P1, the outside pressure 130 P0, the temperature T, the volume V, the change of volume 160 $\Delta V$, the change of mass $\Delta m$, the surface area A, the permeability $\varepsilon$, a thickness of a membrane 120 $\delta$ and time t, as:

$$\varepsilon = [\Delta V \delta]/[A t (P1 - P0)] \quad (1)$$

For example if air is used, which has a molecular weight of 4.817E-26 Kg/molecule, a density p of 1.29 kg/m^3, a temperature of 20 C or 293K, a radius of 7 mm, an internal pressure P1=1.2 atm, and outside pressure of P0=1.0 atm, a surface area of 6.15 cm^2, a thickness of a balloon $\delta$=0.002 inch or 0.005 cm, where the pressure drops from 1.2 atm to 1.0 atm in t=8 hours, a permeability value $\varepsilon$ of $$\varepsilon = 1.24E\text{-}10 \text{ cm}^\wedge 3/(s \text{ cm}^\wedge 2 \text{ cmHg}) \quad (2)$$

is obtained. Thus materials that have an equivalent permeability or less will satisfy the design criteria. For example butyl rubber, polystyrene, polyethylene high density, nylon 6, and Teflon and other like materials.

FIGS. 2A and 2B illustrate a generic variable volume inflatable element attached to a reservoir and a stent. FIG. 2A illustrates a non-inflated variable volume balloon having an uninflated volume 220 V1, having an uninflated internal pressure of 150 P1 and an outside pressure of 130 P0. The variable volume balloon can be attached to a reservoir having a pump volume 230 V2. The reservoir can be reduced starting at time t=t0 to a final volume 240 V3 (FIG. 2B) at time t=t1. The decrease of the reservoir volume moves fluid into the variable volume balloon 210, increasing the volume 270 V4, where the radius has increased to 250 R4 and the internal pressure increases to 260 P3. If one assumes an initial volume V1 about 0, V3 about 0, and P1=P0, then one can solve for the volume V4 and the pressure P3 as:

$$V2=(P3*V4)/P1 \quad (3a)$$

$$P3=P1+[(2\sigma)/R4] \quad (3b)$$

Where σ is the surface tension of the expanded inflation element. For example if one wishes to have V4=1000 mm^3, P3=1.2 atm and P0=1.0 atm, then V2=1.2 cm^3.

FIGS. 3A and 3B illustrate a generic constant volume inflatable element attached to a reservoir and a stent. In FIG. 3A, the constant volume inflatable element has an initial volume 305 V1, an internal pressure 365 P1 and an outside pressure 130 P0. At time t=t0, the reservoir has a pump volume 330 V2. The reservoir can be reduced to a final volume 340 V3 at time t=t1 (FIG. 3B). The decrease of the reservoir volume moves fluid into the variable volume balloon 310, increasing the volume 370 V4, where the radius has increased to 350 R4 and the internal pressure increases to 360 P3. Assuming that the initial volume 305 V1 is not 0, that 370 V4 is not 0, that 305 V1 is not equal to 370 V4, the reservoir volume 330 V2 can be calculated as:

$$V2=[(P3*V4)/P1]-V1 \quad (4)$$

If one assumes that the balloon 310 (inflatable element) is a constant volume, thus V1 is about =V4, then the reservoir volume needed can be expressed as:

$$V2=[(P3*V4)/P1]-V4 \quad (5)$$

For example if one designs V4=1000 mm^2, an internal pressure 1.2 atm, an outside pressure of 1.0 atm, one can obtain V2=0.2 cm"3.

Figure 4B:
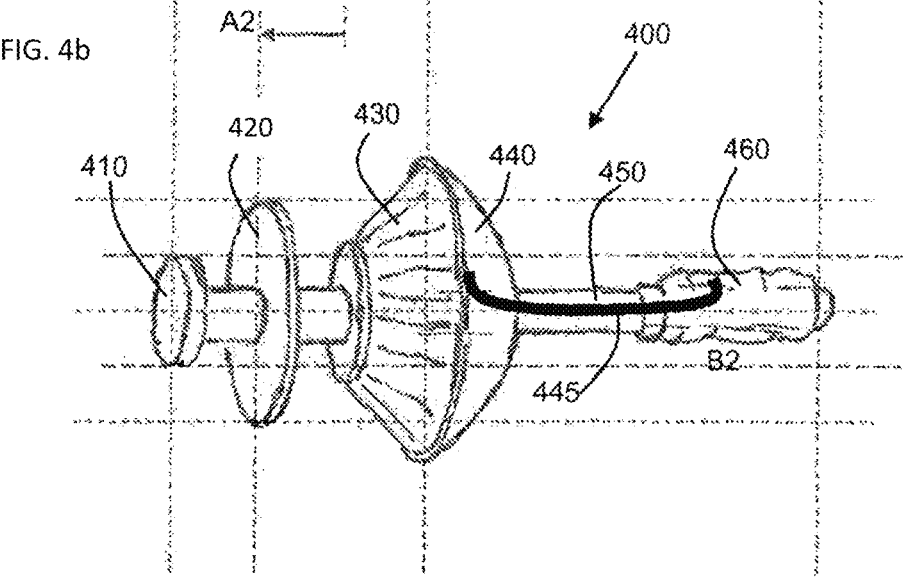

FIGS. 4a and 4b illustrate an earplug 400 including an inflatable element 460 attached to a reservoir (e.g., a chamber enclosed by an elastic membrane 430 and a stop flange body 440) and a stent 450, where an elastic membrane 430 provides a pressurizing force in accordance with at least one exemplary embodiment. FIG. 4a illustrates the earplug 400 with an inflated B1 inflation element 460. FIG. 4b illustrates a deflated B2 inflation element 460. For example when a moveable plate 420 in a first position A1 is pulled to position A2, fluid from the inflated inflation element 460 flows into the reservoir via an inflation channel 445, where the elastic membrane 430 provides a restoring and in this example a pressurizing force. In the operation of the exemplary embodiment a thumb can be placed on knob 410 while a finger pulls moveable plate 420.

Figure 5A:
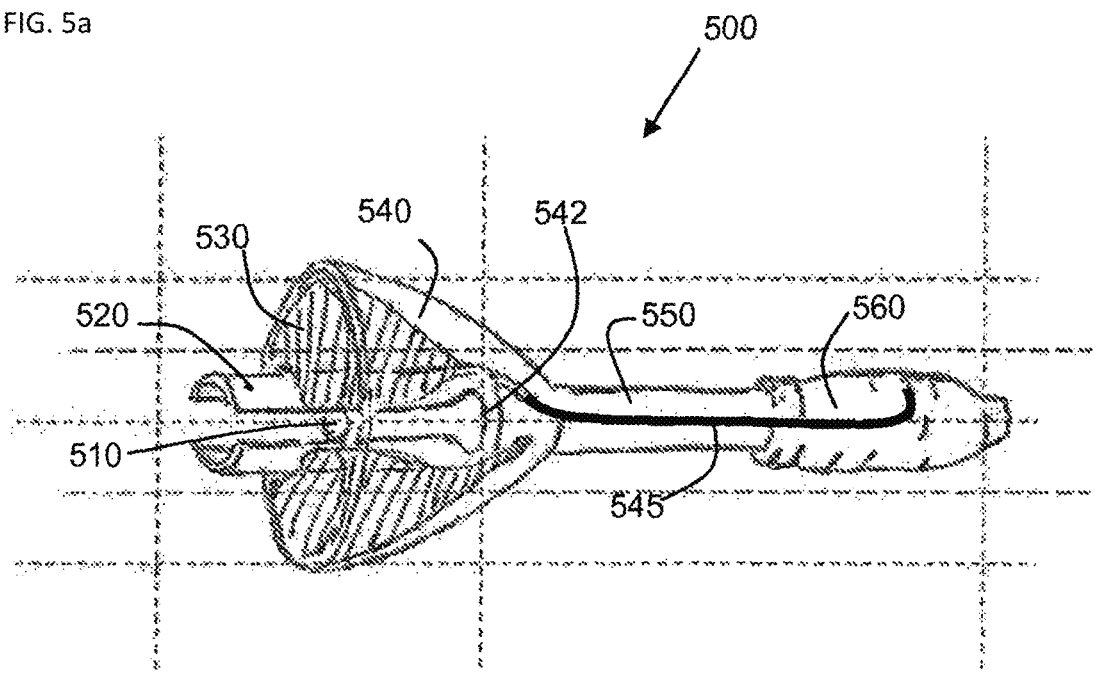
FIGS. 5a and 5b illustrate an earplug including an inflatable element attached to a reservoir and a stent, using a pinchable resilient member to provide a pressurizing force in accordance with at least one exemplary embodiment.
Figure 5B:
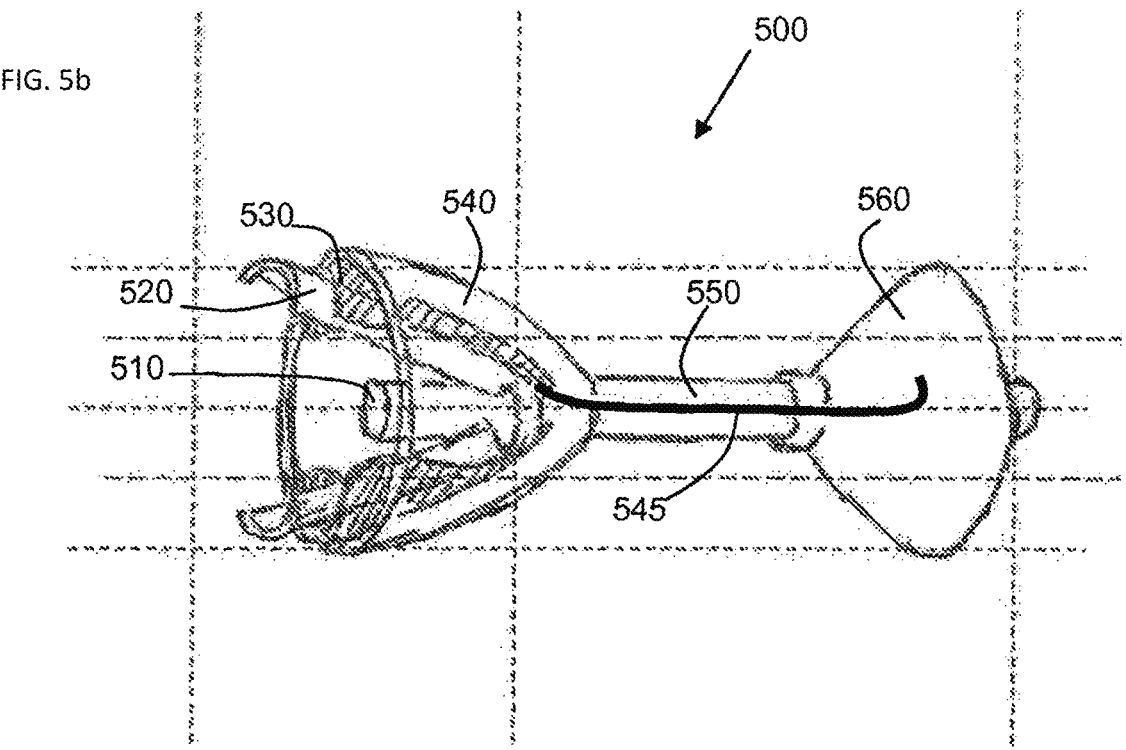

FIGS. 5a and 5b illustrate an earplug 500 including an inflatable element 560 attached to a reservoir 530 and a stent 550, using a pinchable resilient member 520 to provide a pressurizing force in accordance with at least one exemplary embodiment. The resilient member 520 can have a portion that provides a restoring force equivalent to a spring constant 542. When the resilient member 520 is pinched reservoir 530 expands moving fluid from the inflation element 560 to the reservoir 530. When the resilient member is unpinched the resilient member 520 presses the reservoir 530 against the stop flange 540 where the fluid moves through the inflation channel 545 into the inflation element 560. A stent 550 with an anti-distal end 510 forms a core that the other elements can be anchored to.

Figure 6A:
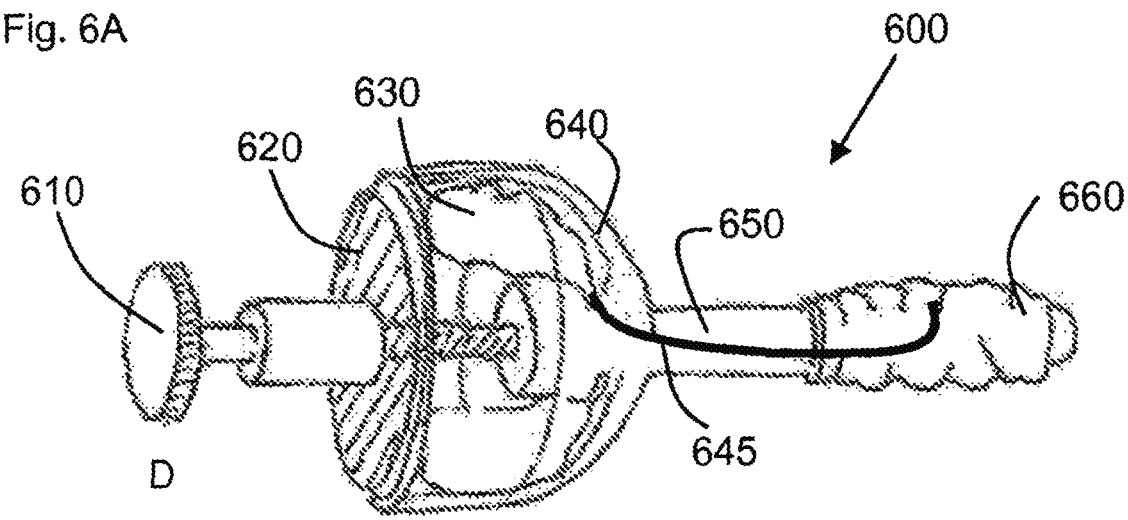
FIGS. 6A and 6B illustrate an earplug including an inflatable element attached to a reservoir and a stent, using a screwable plate to provide an adjustable pressurizing force in accordance with at least one exemplary embodiment.
Figure 6B:
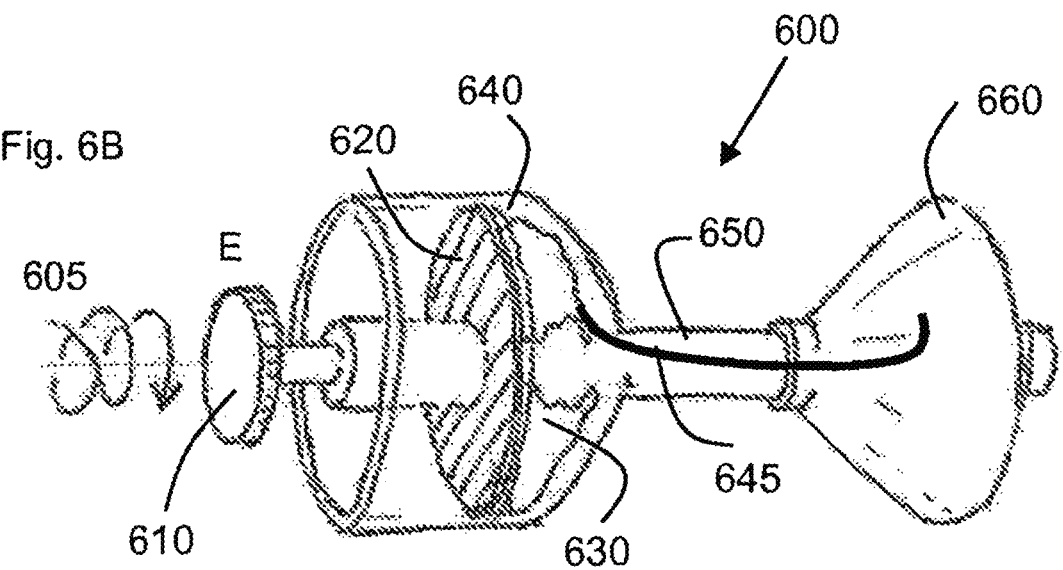

FIGS. 6A and 6B illustrate an earplug 600 including an inflatable element 660 attached to a reservoir 630 and a stent 650, using a screwable 605 plate 620 to provide an adjustable pressurizing force in accordance with at least one exemplary embodiment. When the knob 610 is moved from position D to position E, plate 620 presses the reservoir 630 against the stop flange 640 to move fluid through the inflation channel 645 into the inflation element 660. A user can use knob 610 to screw clockwise and anti-clockwise to adjust the deformation of reservoir 630 to move fluid in and out of inflation channel 645 to inflate the inflation element 660.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and function.

What is claimed is:

1. An earpiece, earphone, earbud or earplug, comprising:
   a reservoir at least partially enclosed by a stop flange and an elastic membrane;
   a having an inflation channel distal section;
   an inflatable element attached to the inflation channel distal section;
   a movable plate coupled to the elastic membrane, wherein moving the movable plate towards the distal section inflates the inflatable element and wherein moving the movable plate away from the distal section stretches the elastic membrane of the reservoir away from the distal section and deflates the inflatable element; wherein the reservoir, the inflation channel, and the inflatable element form a closed pneumatic system containing a fluid;
   wherein the reservoir is attached to the inflation channel and being seperate from the inflatable element;
   wherein the elastic membrane is configured to provide a force to maintain an expansion of the inflatable element; and
   wherein the elastic membrane is configured such that stretching the elastic membrane of the reservoir away from the distal section moves the fluid through the inflation channel from the inflatable element to the reservoir deflating the inflatable element.

2. The earpiece, earphone, earbud or earplug of claim 1, wherein the inflatable element is pressurized to a gauge pressure range from 0.05 bar to 0.25 bar for a given fluid used within the inflatable element.

3. The earpiece, earphone, earbud or earplug of claim 1, wherein the inflatable element is composed of a permeable material so that less than 0.1 bar gauge pressure is leaked in 12 hours.

4. The earpiece, earphone, earbud or earplug of claim 1, wherein the inflation channel is made of a material of a predetermined permeability and a material of the inflatable element is of a given permeability such that an inflation pressure drops from 1.2 atmospheres to 1 atmospheres in a 8 hour time period after the inflatable element is initially pressurized to 1.2 atmospheres.

5. The earpiece, earphone, earbud or earplug of claim 1, wherein the inflatable element is a balloon or bladder.

6. The earpiece, earphone, earbud, or earplug of claim 1, where the fluid in the reservoir is a liquid.

7. The earpiece, earphone, earbud or earplug of claim 1, wherein the inflatable element is a constant volume balloon.

8. The earpiece, earphone, earbud or earplug of claim 1, wherein the inflatable element is a variable volume balloon.

9. The earpiece, earphone, earbud or earplug of claim 1, wherein the reservoir of fluid comprises a volume encompassed by the stop flange and the elastic membrane.

10. The earpiece, earphone, earbud or earplug of claim 1, wherein the inflatable element is made of a material having a durometer of 50 Shore or less.

11. The earpiece, earphone, earbud or earplug of claim 1, wherein the elastic membrane that provides the pressuring force is made of a material having a durometer of 50 Shore or less.

12. The earpiece, earphone, earbud or earplug of claim 1, wherein the inflatable element is made of one of butyl rubber, polystyrene, polyethylene high density, or nylon 6.

13. The earpiece, earphone, earbud or earplug of claim 1, wherein the inflatable element is made of a material having a durometer that is less than a durometer of the elastic membrane.

* * * * *